United States Patent
Kim et al.

(10) Patent No.: US 7,364,743 B2
(45) Date of Patent: Apr. 29, 2008

(54) NUCLEOTIDE SEQUENCE ENCODING PTD AND CEA FUSION PROTEIN, TAT-CEA FUSION PROTEIN, ANTI-TUMOR VACCINE AND PHARMACEUTICAL COMPOSITION FOR TREATING TUMOR COMPRISING THE FUSION PROTEIN

(75) Inventors: Tai-gyu Kim, Seoul (KR); Hyun-il Cho, Seoul (KR); Chang-hyeok An, Eujeongbu-si (KR); Won-kyung Kang, Seoul (KR); Seong-taek Oh, Seoul (KR)

(73) Assignee: Catholic University Industry Academic Cooperation Foundation, Seoul (KR)

( * ) Notice: Subject to any disclaimer, the term of this patent is extended or adjusted under 35 U.S.C. 154(b) by 0 days.

(21) Appl. No.: 10/880,847

(22) Filed: Jun. 29, 2004

(65) Prior Publication Data

US 2005/0288214 A1  Dec. 29, 2005

(51) Int. Cl.
*A61K 39/00* (2006.01)
(52) U.S. Cl. .............................. 424/192.1; 424/184.1; 424/185.1; 435/320.1
(58) Field of Classification Search ............... 530/350; 514/2
See application file for complete search history.

(56) References Cited

U.S. PATENT DOCUMENTS

| 2002/0142299 A1 | 10/2002 | Davidson et al. |
| 2003/0211590 A1 | 11/2003 | Hwu |
| 2004/0002455 A1* | 1/2004 | Uger et al. .................... 514/12 |
| 2004/0249126 A1* | 12/2004 | Celis .......................... 530/350 |

OTHER PUBLICATIONS

He et al (International Journal of Biochemistry and Cell Biology, 2005, 37:192-205).*
Gura (Science, 1997, 278:1041-1042).*
Jain (Sci. Am., 1994, 271:58-65).*
Curti (Crit. Rev. in Oncology/Hematology, 1993, 14:29-39).*
Stedman's Medical Dictionary. p. 1.*
Shiloh et al (Eur. J Biocehm, 2002, 269:494-501).*
Curti (Crit. Rev. in Oncology/Hematology, 1993, 14:29-39) t.*
"Enhanced Induction of CEA Specific Tumor Immunity by TatCEA Fusion Protein." J Korean Soc Coloprotol vol. 19, No. 3, Jun. 30, 2003, pp. 121-128.

* cited by examiner

*Primary Examiner*—Susan Ungar
*Assistant Examiner*—Laura B Goddard
(74) *Attorney, Agent, or Firm*—Brinks Hofer Gilson & Lione (57) ABSTRACT

A nucleotide sequence encoding a fusion protein of PTD and CEA. The nucleotide sequence includes a CEA-encoding nucleotide sequence into which a PTD-encoding nucleotide sequence is inserted.

3 Claims, 3 Drawing Sheets

1. LOVO
2. 293EBNA
3. 293EBNA/CEA
4. 293EBNA/TatCEA

Protein extracts of 10^5 dendritic cells were analyzed by 8% SDS-PAGE gel and subjected to western blot analysis with an anti-CEA antibody.

FIG.3

CEA          TatCEA

FIG. 4

DC/cont        DC/CEA        DC/TatCEA

FIG. 5

NUCLEOTIDE SEQUENCE ENCODING PTD AND CEA FUSION PROTEIN, TAT-CEA FUSION PROTEIN, ANTI-TUMOR VACCINE AND PHARMACEUTICAL COMPOSITION FOR TREATING TUMOR COMPRISING THE FUSION PROTEIN

BACKGROUND OF THE INVENTION

1. Field of the Invention

The present invention relates to an anti-tumor immune response, and in more detail, to a method for inducing immune responses specific to tumor associated antigen that acts specifically on tumor cells.

2. Description of the Related Art

In the current cancer treatment, after cancer tissues are removed as much as possible, the remaining cancer cells are killed by radiotherapy and chemotherapy. This is a main method to treat tumors currently. But surgery has several problems like that the removal range is broad and there is recurrent risk by micrometastasis. Radiotherapy and chemotherapy also have many side effects. Especially, in the case of anti-tumor drugs, they are always not effective in all cancer. In many cases, remaining cancer cells that were exposed to anticancer drug have resistance, keep on growing and metastasize to other organs. In the result, the cancer is impossible to be treated.

Accordingly, we have no choice but to admit that there is the limit to conquer cancer by only these therapies. Therefore, immune therapy is now expected as a new cancer treatment, which uses immunity of our body.

The immune therapy has side effects less than other treatments and is more effective in being used in combination with other treatments. So importance of immune therapy is currently revealed. Immune therapy is indirect treatment that treats cancer by activating patient's immune response whereas surgery, chemotherapy and radiotherapy directly attack cancer cells among cancer treatments.

Broadly, the different types of immune response fall into two categories: a humoral immune response and a cell-mediated immune response. The humoral immune systems have a function to make antibodies for degradation and removal of antigens, e.g. infectious microbes, virus and bacteria, invading into the human body. Meanwhile, the cellular immune response relates to immune surveillance mechanism and produces cells (lymphocytes) specific to any antigens.

The cellular immune responses are more important in the tumor-related immunity rather than the humoral immune systems. Like this, antitumor immune response is generally related to cell-mediated responses; therefore it is known that the role of CD8+ cytotoxic T lymphocyte, CTL is important for this reaction. Nowadays, tumor-associated antigen (TAA) has been studied to induce antitumor T cell. Also, the researches for T cell immune therapy against tumor have been continued according to development of recombinant DNA technology.

To induce the antigen-specific cytotoxic T lymphocyte specifically acting to the tumor cell, the presentation of antigen to MHC class 1 molecule is essential. This pathway is initiated as that treatment of large multifunctional proteasome to cellular protein is carried out. And then the antigen was transported into the endoplasmic reticulum through transporter protein associated with antigen processing, bounded with MHC class 1 molecules, and presented to cell surface throughout the golgi apparatus.

But it is characterized that presentation pathway of antigen by MHC class 1 molecule appears only within the cell. So, there has been some tries to directly introduce external protein into MHC class I. Generally, protein introduced for vaccine is known inadaptable to increase antitumor immune response, because it enters into the cell through endocytosis and then stimulates Th(CD4+) cell presented by MHC class II molecules. In the result, it activates humoral immune response instead of cellular immune response.

Therefore, there has been a requirement toward a method for enabling the externally introduced antigen protein to transport into cytoplasm of antigen presentation cell and then the antigen is presented by MHC class I molecules.

SUMMARY OF THE INVENTION

The present invention provides a nucleotide sequence encoding the fusion proteins of PTD and CEA, the nucleotide sequence comprising a CEA-encoding nucleotide sequence into which a PTD-encoding nucleotide sequence is inserted. The PTD-encoding nucleotide sequence may be a nucleotide sequence encoding a HIV Tat protein, and especially, a sequence encoding 47~57 amino acid residues of Tat protein.

The present invention also provides a recombinant vector comprising the CEA-encoding nucleotide sequence to which a PTD-encoding nucleotide sequence is inserted and further provides a TatCEA fusion protein generated from the recombinant vector.

In addition, the present invention provides an anti-tumor vaccine and a pharmaceutical composition comprising the TatCEA fusion protein for treating tumor.

Furthermore, the present invention provides method for inducing CEA-specific anti-tumor immune response by using the TatCEA fusion protein.

DESCRIPTION OF THE PREFERRED EMBODIMENTS

The present invention is described in detail below.

Among therapies for treating tumor, the present invention is based on immune therapy of identifying peptide epitope originated from tumor-antigen and then treating the tumor by using cytotoxic T cell specific to the tumor-antigen. To induce cytotoxic T cell specific to tumor cells, adequate tumor-related antigen(TAA) should be selected. Tumor-related antigen may be prostate-specific antigen, HER-2/ neu, MUC-1, point mutated or wild-type overexpressed p53, MAGE antigen and CEA(carcinoembryonic antigen) and so on.

CEA is a 180 kDa oncofetal glycoprotein and soluble tumor marker. CEA is expressed over 95% in colorectal, gastric and pancreatic carcinomas, in approximately 50% of breast cancer, and in 70% of non-small cell lung cancers.

In the present invention, CEA is used as tumor related antigen since it may be powerful target TAA for tumor immune therapy. It is believed that dendritic cells in the present invention generate CEA-specific cytotoxic T cell and as result, the cytotoxic T cells are effective against several tumors.

In the present invention, inventors use PTD(Protein Transduction Domain) that has a characteristic to enable external proteins to be transduced into cytoplasm for MHC class I antigen presentation pathway of tumor-associated antigen. Any kind of PTD having such an ability to transduce external proteins may be used, however, Tat protein may be most preferable among those.

Tat protein is a kind of controlling protein of HIV. It transduces a cell that is infected with HIV in the exo-cell environment, and then activates HIV in the latent period by activating each gene expression. HIV Tat(transactivator of transcription) protein is composed of N-terminal domain, cystein rich domain, core domain, basic domain and 5$^{th}$ domain. HIV Tat protein acts as a chemokine and induces chemotaxis of monocytes. HIV Tat protein is transported into cytoplasm without a process of endocytosis into cell due to a region encoding amino acid residues 49 to 57 of the Tat protein (RKKRRQRRR) (SEQ ID: 5). Tat protein transported into the cytoplasm goes through a protein lysis pathway in the cytoplasm. Fragments of Tat protein bind to MHC class I molecules in the ER(endoplasmic reticulum) and these complexes are presented to the cell surface. Because of these characteristics, HIV Tat protein may be used preferably in this present invention in order to induce cell-toxicity T cell immune response only for MHC class I molecule against tumor antigens.

To produce the PTD and CEA fusion proteins, the present invention provides a nucleotide sequence encoding the fusion proteins of PTD and CEA, the nucleotide sequence comprising a CEA-encoding nucleotide sequence into which a PTD-encoding nucleotide sequence is inserted.

Especially, the present invention provides a nucleotide sequence encoding TatCEA fusion protein. The nucleotide sequence encoding HIV Tat may be a sequence encoding 47~57 amino acids residues of Tat protein. Also, the nucleotide sequence may be inserted into the position next to 883rd nucleotide in central region of CEA, and the nucleotide sequence encoding TatCEA fusion protein is represented in SEQ ID: 1 as follows:

```
                                                              <SEQ ID: 1>
           atggagtctc cctcggcccc tccccacaga tggtgcatcc cctggcagag gctcctgctc     60
acagcctcac ttctaacctt ctggaacccg cccaccactg ccaagctcac tattgaatcc    120
acgccgttca atgtcgcaga ggggaaggag gtgcttctac ttgtccacaa tctgccccag    180 catcttttg  gctacagctg gtacaaaggt gaaagagtgg atggcaaccg tcaaattata    240
ggatatgtaa taggaactca acaagctacc ccagggcccg catacagtgg tcgagagata    300 atataccca  atgcatccct gctgatccag aacatcatcc agaatgacac aggattctac    360
accctacacg tcataaagtc agatcttgtg aatgaagaag caactggcca gttccgggta    420
tacccggagc tgcccaagcc ctccatctcc agcaacaact ccaaacccgt ggaggacaag    480
gatgctgtgg ccttcacctg tgaacctgag actcaggacg caacctacct gtggtgggta    540
aacaatcaga gcctcccggt cagtcccagg ctgcagctgt ccaatggcaa caggaccctc    600
actctattca atgtcacaag aaatgacaca gcaagctaca aatgtgaaac ccagaaccca    660
gtgagtgcca ggcgcagtga ttcagtcatc ctgaatgtcc tctatggccc ggatgccccc    720
accatttccc ctctaaacac atcttacaga tcaggggaaa atctgaacct ctcctgccac    780
gcagcctcta acccacctgc acagtactct tggtttgtca atgggacttt ccagcaatcc    840
acccaagagc tctttatccc caacatcact gtgaataata gtggatctta tggaaggaag    900
aagcggagac agcgacgaag agggatccta tacgtgccaa gcccataact cagacactgg    960
cctcaatagg accacagtca cgacgatcac agtctatgca gagccaccca aaccettcat   1020 caccagcaac aactccaacc ccgtggagga tgaggatgct gtagccttaa cctgtgaacc   1080
tgagattcag aacacaacct acctgtggtg ggtaaataat cagagcctcc cggtcagtcc   1140
caggctgcag ctgtccaatg acaacaggac cctcactcta ctcagtgtca caaggaatga   1200
tgtaggaccc tatgagtgtg gaatccagaa cgaattaagt gttgaccaca gcgacccagt   1260
catcctgaat gtcctctatg gcccagacga ccccaccatt tcccctcat  acacctatta   1320 ccgtccaggg gtgaacctca gcctctcctg ccatgcagcc tctaacccac ctgcacagta   1380
```

-continued

```
ttcttggctg attgatggga acatccagca acacacacaa gagctcttta tctccaacat    1440
cactgagaag aacagcggac tctatacctg ccaggccaat aactcagcca gtggccacag    1500
caggactaca gtcaagacaa tcacagtctc tgcggagctg cccaagccct ccatctccag    1560
caacaactcc aaaccgtgg aggacaagga tgctgtggcc ttcacctgtg aacctgaggc    1620
tcagaacaca acctacctgt ggtgggtaaa tggtcagagc ctcccagtca gtcccaggct    1680
gcagctgtcc aatggcaaca ggaccctcac tctattcaat gtcacaagaa atgacgcaag    1740
agcctatgta tgtggaatcc agaactcagt gagtgcaaac cgcagtgacc cagtcaccct    1800
ggatgtcctc tatgggccgg acaccccat catttccccc ccagactcgt cttacctttc    1860
gggagcgaac ctcaacctct cctgccactc ggcctctaac ccatcccgc agtattcttg    1920 gcgtatcaat gggataccgc agcaacacac acaagttctc tttatcgcca aaatcacgcc    1980
aaataataac gggacctatg cctgttttgt ctctaacttg gctactggcc gcaataattc    2040
catagtcaag agcatcacag tctctgcatc tggaacttct cctggtctct cagctggggc    2100
cactgtcggc atcatgattg gagtgctggt tggggttgct ctgatatag               2149
```

This present invention also provides a vector containing the nucleotide sequence encoding TatCEA fusion protein, which is engineered to express the TatCEA fusion proteins.

Figure 1:
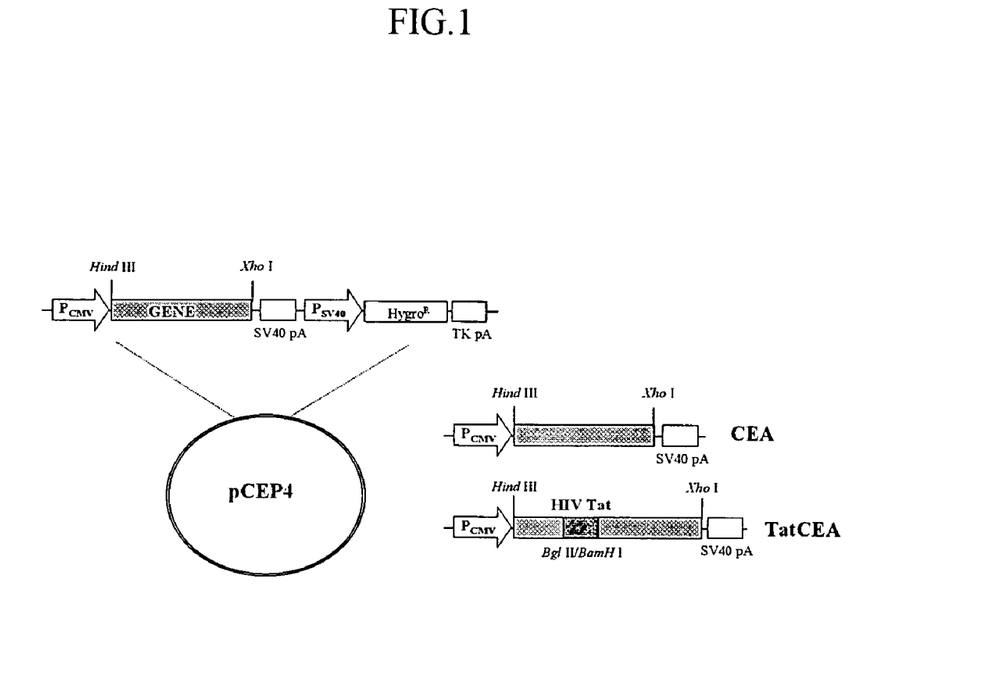
FIG. 1 shows the map of recombinant plasmid, pCEP4-CEA and pCEP4-TatCEA.

The preparations of the nucleotide sequence encoding TatCEA fusion protein and recombinant vectors containing the nucleotide sequence were carried out as described in Example 1. A map of the recombinant vectors according to the present invention is shown in FIG. 1.

Figure 2:
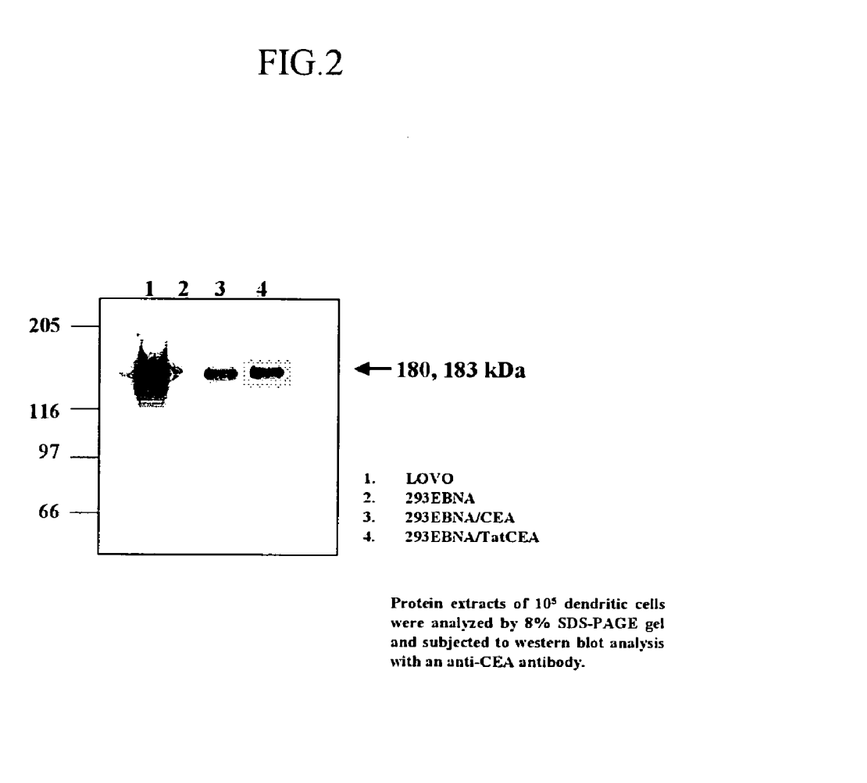
FIG. 2 shows the result of western blot analysis which was performed for expression of pCEP4-CEA and pCEP4-TatCEA in 293EBNA cell line.

The present invention also provides a TatCEA fusion protein that is generated from the recombinant vector containing the nucleotide sequence encoding TatCEA fusion protein. The expression of the fusion protein was determined by western blot. TatCEA fusion protein was about 183 kDa as shown in FIG. 2. The transduction activity of the fusion protein was determined by immunofluorescence microscopy and it demonstrated that TatCEA mainly migrated into cytoplasm.

In addition, the present invention provides a method for inducing a CEA-specific anti tumor immune response using the TatCEA fusion proteins. Dendritic cells may be used as antigen-presenting cells in the present invention. IFN-γ ELISPOT assay was used to estimate CEA-specific cell immune activity of TatCEA fusion protein. IFN-γ, known as a representative cytokine of Th-1, is generated from T cells activated by antigen or mitogen stimulus and is secreted as an antigen specific T cell response to peptides presented by MHC class I. IFN-γ is a factor for estimating the effect of inducing a cellular immune response. In the IFN-γ ELISPOT assay, which directly estimates a frequency of T cells responding specifically to an antigen, it is revealed that the dendritic cells pulsed by TatCEA induce the cellular immune response more effectively than the dendritic cells pulsed by CEA.

The present invention further provides an anti-tumor vaccine and a pharmaceutical composition for treating a tumor, which comprise the TatCEA fusion protein. They can function as an anti-tumor vaccine or a pharmaceutical composition for treating a tumor, which is against several kinds of tumors not limited to a specific kind of tumor, since the anti-tumor vaccine and the pharmaceutical composition for treating tumors according to the present invention can induce CEA-specific immune response.

EXAMPLES

The present invention is described in more detail in the following Examples, but it should be understood that the examples are intended to illustrate the present invention, but not limit the invention.

Cell Lines and Method of Cultivation

All cell lines and the methods of cultivation in following examples are as below. 293EBNA cell line, expressing EBNA protein, and 293EBNA/CEA, expressing CEA, and 293EBNA/TatCEA, expressing TatCEA, were cultured in DMEM (Gibco BRL) supplemented with 2 mL L-glutamine and 10% FBS (fetal bovine serum; Gibco BRL) at 37° C. in 5% $CO_2$ incubator. Mouse T cell lymphoma EL-4 cells (ATCC) were cultured in DMEM produced by upper method.

Statistical Analysis

Results of all measurement accomplished in the following examples were expressed as mean±standard deviation and were analyzed with Student's t-test. Data were taken as statistically significant at $P<0.05$.

Example 1

Cloning of CEA and TatCEA Fusion Gene and their Expression

Preparation of TatCEA Fusion Gene and its Cloning

After the following double stranded nucleotide was synthesized to amplify HIV Tat gene, it was restricted with Bgl II and BamH I restriction enzyme. And then the fragments of HIV Tat were centrifuged in 2% agarose gel and isolated by using Gel extraction kit (QIAGEN, Germany).

HIV Tat nucleotide sequence:

CCTGAGATCTTATGGAAGGAAGAAGCGGAGACAGCGA (SEQ ID NO:2)
CGAAGAGGATCCTTAC

CEA gene was amplified by PCR method from cDNA isolated from LoVo cell line (ATCC# CCL-229), human colon cancer tumor cell line, using sense and antisense primer.

sense primer
(5'-TACAAAGCTTATGGAGTCTCCCTCGGC-3') (SEQ ID NO:3)

antisense primer
(5'-CCTTCTCGAGCTATATCAGAGCAACCCC-3') (SEQ ID NO:4)

After the amplified CEA gene was restricted by Hind III and Xho I, it was inserted into pCEP4 plasmid vector (Invitrogen. Inc.) restricted by the same restriction enzymes. After isolated Tat gene was restricted with Bgl II and BamH I, it was inserted in next to 883rd nucleotide, central region of CEA which restricted by BamH I The recombinant pCEP4 plasmid vector with TatCEA gene and pCEP4 plasmid vector with only CEA gene were cloned.

FIG. 1 shows map of recombinant plasmid, pCEP4-CEA and pCEP4-TatCEA constructed as above. The direction of transcription is indicated by arrows. Restriction endonuclease sites containing EcoR I, BamH I and Bgl II cloning site are shown.

Expression of TatCEA Fusion Protein and Determination of Ability to Transduce Protein To produce TatCEA fusion protein and CEA protein, the recombinant pCEP4-CEA and pCEP4-TatCEA plasmid were transduced into human fetal kidney cell line, 293EBNA(Clontech.). After that, they were established into stable cell lines selected by hygromycin treatment. Protein extracts of cell lysates were analyzed by SDS-PAGE on 8% acrylamide gel and subjected to western blot analysis with anti-CEA antibodies. As shown from FIG. 2, CEA was expressed at 180 kDa and TatCEA at 183 kDa from western blot analysis, To investigate an ability to transduce protein to dendritic cells, fixed dendritic cells pulsed with CEA and TatCEA for 10 min. were subjected to fluorescent staining with CEA-specific monoclonal antibodies. Dendritic cells were cultured for 10 days and were pulsed with CEA (A) and TatCEA (B) at the ratio 1:1 at 37° C. for 2 hr.

Figure 3:
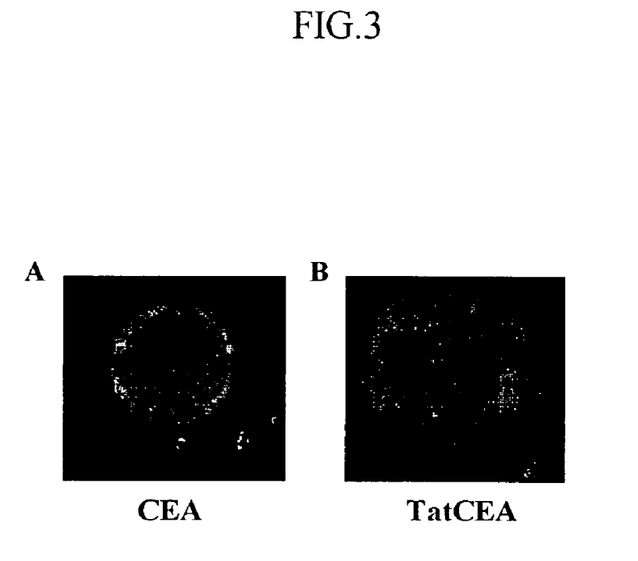
FIG. 3 shows the results of immunofluorescent staining for expression of CEA in CEA (A) or TatCEA (B)-pulsed dendritic cells.

FIG. 3 shows the result of immunofluorescent staining to confirm whether CEA was expressed in CEA or TatCEA-pulsed dendritic cells. As shown from FIG. 3, it was confirmed that CEA was on the cellular surface and TatCEA migrated into cytoplasm. (FIG. 3)

Example 2

Immunity using Dendritic Cells Pulsed with CEA and TatCEA Fusion Protein

To culture dendritic cells from experimental mice, bone marrow was isolated from female C57BL/6 (6~8 weeks) mice. T-cells, B-cells, and macrophages were removed from the isolated bone marrow cells. Dendritic cells were cultured in RPMI 1640 medium (Gibco BRL.) supplemented with 100 ng/ml GM-CSF (Genzyme) and 500 U/ml IL-4 (Genzyme) for 7 days. Dendritic cells were pulsed with TatCEA fusion protein and CEA protein at several concentrations and were reacted at room temperature for 10 min. Fluorescent staining was observed by fluorescence microscopy or the transduction of protein was determined by using a fluorescence spectrometer.

The dendritic cells ($5 \times 10^5$/mouse) that were treated with CEA fusion protein or TatCEA fusion protein at the appropriate concentration were injected intravenously into each of four mice in each experimental group. The dendritic cells untreated with protein were injected to a control group. After a first intravenous injection of dendritic cells, mice were re-injected 2 weeks later. Humoral and cellular immune responses were detected after 2 weeks of reinjection.

Example 3

Estimation of CEA Specific Cellular Immune Response Through Measuring Frequency of INF-γ Expression Lymphocytes by ELISPOT To measure effect of inducing cellular immune response by dendritic cells pulsed with CEA and TatCEA, spleen cells were isolated from immunized mice. The spleen cells were stimulated with dendritic cells pulsed with CEA peptide (EAQNTTYL) (SEQ ID: 6) in vitro and the frequency of IFN-γ expression lymphocytes was measured.

The dendritic cells isolated from the mice were cultured for 1 week and they were pulsed with CEA peptide of 10 ug/ml. The pulsed dendritic cells were used as antigen presenting cells. 96-well plates were prepared by coating the plates with a murine monoclonal IFN-γ capture antibody. Spleen cells of immune injected mice were isolated and red blood cells were removed.

The spleen cells were mixed with dendritic cells pulsed with CEA peptide in equal volume (1:1) in the 96-well plate at a concentration of $1 \times 10^4$/well. The spleen cells mixed with the dendritic cells were reacted at 37° C. for 24 hr in a 5% $CO_2$ incubator. After 24 hrs. the plates were washed with PBS (phosphate-buffer saline)/Tween (0.05%) 3 times. Biotinylated anti IFN-γ Abs (2 ug/ml) were added to the wells of the 96-well plates and were reacted at room temperature for 2 hr. After 4 times washing, avidin/alkaline phosphatase was added and reacted at room temperature for 1 hr and the number of spots in each well were measured by using ELISPOT Reader System (AID).

Figure 4:
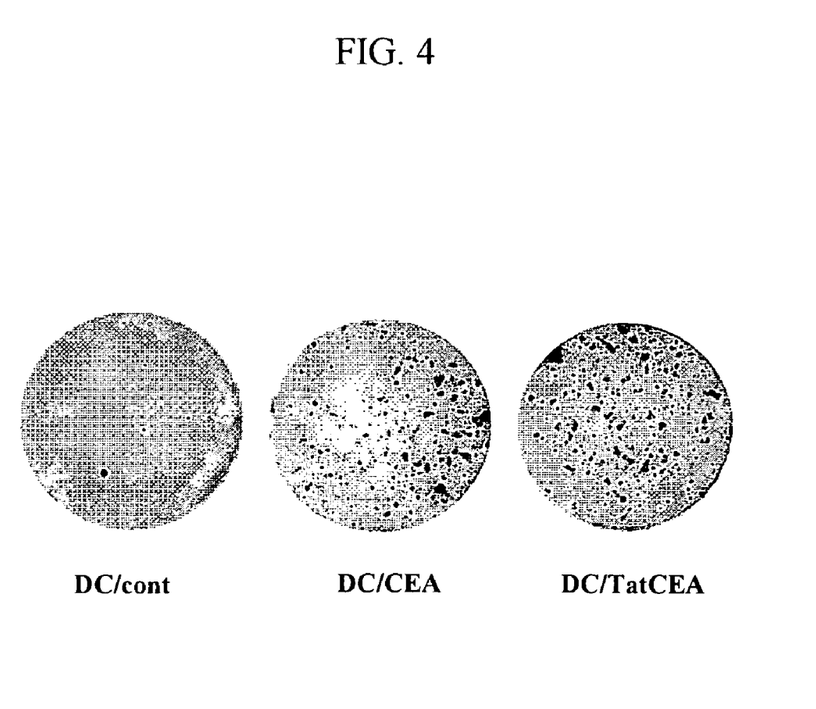
FIG. 4 shows the results of detection of antigen-specific CD8+ T cells by ELISPOT in the spleen cells of mice immunized with dendritic cells pulsed with 293EBNA/CEA and 293EBNA/TatCEA cell lysates.
Figure 5:
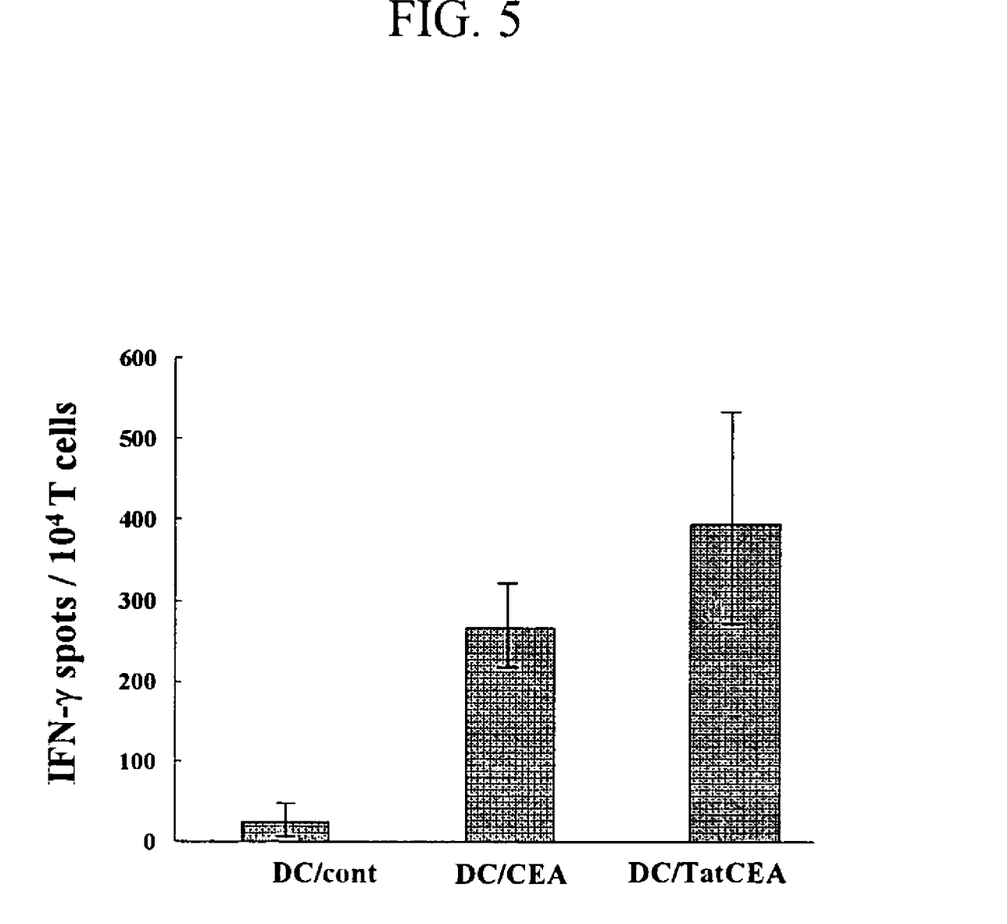
FIG. 5 shows the results of IFN-γ ELISPOT assay performed to determine whether dendritic cells pulsed by CEA peptide induce CEA specific CD8+ T cell response.

Results showed the frequency of IFN-γ expression in lymphocytes was increased significantly as $322 \pm 28.2/10^4$ lymphocytes in dentritic cells pulsed with TatCEA ($p<0.0001$), compared to $14.5 \pm 4.5/10^4$ lymphocytes in dentritic cells un-pulsed with CEA (control group), and $244 \pm 29.5/10^4$ lymphocytes in dentritic cells pulsed with CEA (FIGS. 4 & 5). In FIG. 5, each bar represents the mean of the results from mice±S.D.

What is claimed is:

1. A TatCEA fusion protein encoded by a recombinant vector comprising the nucleotide sequence shown in SEQ ID NO: 1; and wherein the TatCEA fusion protein induces an immune response.

2. A method for inducing an immune response using comprising administering to a mammal dendritic cells pulsed with the TatCEA fusion protein according to claim 1 to induce the immune response.

3. The TatCEA fusion protein of claim 1, wherein the nucleotide sequence is amplifiable by polymerase chain reaction with primers SEQ ID NOS: 3 and 4.

* * * * *

UNITED STATES PATENT AND TRADEMARK OFFICE
CERTIFICATE OF CORRECTION

PATENT NO.       : 7,364,743 B2  
APPLICATION NO.  : 10/880847  
DATED            : April 29, 2008  
INVENTOR(S)      : Tai-gyu Kim et al.

It is certified that error appears in the above-identified patent and that said Letters Patent is hereby corrected as shown below:

Column 11, in claim 2, line 1, after "immune response" delete "using".

Signed and Sealed this

Second Day of September, 2008

JON W. DUDAS  
*Director of the United States Patent and Trademark Office*

SEQUENCE LISTING

<160> NUMBER OF SEQ ID NOS: 4

<210> SEQ ID NO 1
<211> LENGTH: 2149
<212> TYPE: DNA
<213> ORGANISM: Artificial Sequence

```
<220> FEATURE:
<223> OTHER INFORMATION: nucleotide sequence of TatCEA fusion protein

<400> SEQUENCE: 1
atggagtctc cctcggcccc tccccacaga tggtgcatcc cctggcagag gctcctgctc      60
acagcctcac ttctaacctt ctggaacccg cccaccactg ccaagctcac tattgaatcc     120
acgccgttca atgtcgcaga ggggaaggag gtgcttctac ttgtccacaa tctgccccag     180 catcttttg gctacagctg gtacaaaggt gaaagagtgg atggcaaccg tcaaattata      240
ggatatgtaa taggaactca acaagctacc ccagggcccg catacagtgg tcgagagata     300
atatacccca atgcatccct gctgatccag aacatcatcc agaatgacac aggattctac     360
accctacacg tcataaagtc agatcttgtg aatgaagaag caactggcca gttccgggta     420
tacccggagc tgcccaagcc ctccatctcc agcaacaact ccaaacccgt ggaggacaag     480
gatgctgtgg ccttcacctg tgaacctgag actcaggacg caacctacct gtggtgggta     540
aacaatcaga gcctcccggt cagtcccagg ctgcagctgt ccaatggcaa caggaccctc     600
actctattca atgtcacaag aaatgacaca gcaagctaca atgtgaaaac ccagaaccca     660
gtgagtgcca ggcgcagtga ttcagtcatc ctgaatgtcc tctatggccc ggatgccccc     720
accatttccc ctctaaacac atcttacaga tcaggggaaa atctgaacct ctcctgccac     780
gcagcctcta cccacctgc acagtactct tggtttgtca atgggacttt ccagcaatcc     840
acccaagagc tctttatccc caacatcact gtgaataata gtggatctta tggaaggaag     900
aagcggagac agcgacgaag agggatccta tacgtgccaa gcccataact cagacactgg     960
cctcaatagg accacagtca cgacgatcac agtctatgca gagccaccca aacccttcat    1020
caccagcaac aactccaacc ccgtggagga tgaggatgct gtagccttaa cctgtgaacc    1080
tgagattcag aacacaacct acctgtggtg ggtaaataat cagagcctcc cggtcagtcc    1140
caggctgcag ctgtccaatg caacaggac cctcactcta ctcagtgtca aaggaatga    1200 tgtaggaccc tatgagtgtg aatccagaa cgaattaagt gttgaccaca gcgacccagt    1260
catcctgaat gtcctctatg gcccagacga cccaccatt tccccctcat acacctatta    1320
ccgtccaggg gtgaacctca gcctctcctg ccatgcagcc tctaacccac ctgcacagta    1380
ttcttggctg attgatggga acatccagca acacacacaa gagctcttta tctccaacat    1440
cactgagaag aacagcggac tctataacctg ccaggccaat aactcagcca gtggccacag    1500
caggactaca gtcaagacaa tcacagtctc tgcggagctg cccaagccct ccatctccag    1560
caacaactcc aaacccgtgg aggacaagga tgctgtggcc ttcacctgtg aacctgaggc    1620
tcagaacaca acctacctgt ggtgggtaaa tggtcagagc ctcccagtca gtcccaggct    1680
gcagctgtcc aatggcaaca ggaccctcac tctattcaat gtcacaagaa atgacgcaag    1740
agcctatgta tgtggaatcc agaactcagt gagtgcaaac cgcagtgacc cagtcacccct    1800 ggatgtcctc tatgggccgg acaccccat catttccccc ccagactcgt cttacctttc    1860
gggagcgaac ctcaacctct cctgccactc ggcctctaac ccatcccgc agtattcttg    1920 gcgtatcaat gggataccgc agcaacacac acaagttctc tttatcgcca aaatcacgcc    1980
aaataataac gggacctatg cctgttttgt ctctaacttg gctactgcc gcaataattc    2040 catagtcaag agcatcacag tctctgcatc tggaacttct cctggtctct cagctggggc    2100
cactgtcggc atcatgattg gagtgctggt tggggttgct ctgatatag                2149

<210> SEQ ID NO 2
```

-continued

```
<211> LENGTH: 53
<212> TYPE: DNA
<213> ORGANISM: Human immunodeficiency virus

<400> SEQUENCE: 2
cctgagatct tatggaagga agaagcggag acagcgacga agaggatcct tac         53

<210> SEQ ID NO 3
<211> LENGTH: 27
<212> TYPE: DNA
<213> ORGANISM: Artificial Sequence
<220> FEATURE:
<223> OTHER INFORMATION: sense primer

<400> SEQUENCE: 3
tacaaagctt atggagtctc cctcggc                                       27

<210> SEQ ID NO 4
<211> LENGTH: 28
<212> TYPE: DNA
<213> ORGANISM: Artificial Sequence
<220> FEATURE:
<223> OTHER INFORMATION: antisense primer

<400> SEQUENCE: 4
ccttctcgag ctatatcaga gcaacccc                                      28
```